(12) United States Patent
Uchida et al.

(10) Patent No.: US 11,813,316 B2
(45) Date of Patent: Nov. 14, 2023

(54) LENTIVIRAL VECTOR FOR TREATING HEMOGLOBIN DISORDERS

(71) Applicant: The United States of America, as represented by the Secretary, Department of Health and Human Services, Bethesda, MD (US)

(72) Inventors: Naoya Uchida, Rockville, MD (US); John F. Tisdale, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 866 days.

(21) Appl. No.: 16/717,420

(22) Filed: Dec. 17, 2019

(65) Prior Publication Data
US 2020/0215167 A1 Jul. 9, 2020

Related U.S. Application Data

(62) Division of application No. 15/510,014, filed as application No. PCT/US2015/045358 on Aug. 14, 2015, now Pat. No. 10,543,257.

(60) Provisional application No. 62/048,881, filed on Sep. 11, 2014.

(51) Int. Cl.
| | |
|---|---|
| *C12N 15/867* | (2006.01) |
| *C12N 15/113* | (2010.01) |
| *C12N 15/12* | (2006.01) |
| *A61K 48/00* | (2006.01) |
| *A61K 38/42* | (2006.01) |
| *C12N 15/86* | (2006.01) |
| *C07K 14/805* | (2006.01) |
| *C12N 7/00* | (2006.01) |

(52) U.S. Cl.
CPC .......... *A61K 38/42* (2013.01); *A61K 48/005* (2013.01); *C07K 14/805* (2013.01); *C12N 7/00* (2013.01); *C12N 15/86* (2013.01); *C12N 2740/16043* (2013.01); *C12N 2830/008* (2013.01); *C12N 2830/46* (2013.01)

(58) Field of Classification Search
None
See application file for complete search history.

(56) References Cited

U.S. PATENT DOCUMENTS

| | | | |
|---|---|---|---|
| 5,861,488 | A | 1/1999 | LeBoulch et al. |
| 6,524,851 | B1 | 2/2003 | Ellis |
| 8,383,404 | B2 | 2/2013 | Yilmaz et al. |
| 2009/0156534 | A1 | 6/2009 | Lisowski et al. |
| 2014/0031412 | A1 | 1/2014 | Vadolas |
| 2015/0216903 | A1* | 8/2015 | Heffner ................ C12N 15/86 435/375 |
| 2018/0223313 | A1 | 8/2018 | Uchida et al. |

FOREIGN PATENT DOCUMENTS

| | | |
|---|---|---|
| WO | WO 2004/054512 A2 | 7/2004 |
| WO | WO 2013/043196 A1 | 3/2013 |
| WO | WO 2014/043131 A1 | 3/2014 |
| WO | WO 2017/059241 A1 | 4/2017 |

OTHER PUBLICATIONS

U.S. Appl. No. 62/236,223, USDHHS, filed Oct. 2, 2015.
Antoniou et al., "The human beta-globin gene contains multiple regulatory regions: identification of one promoter and two downstream enhancers," *EMBO J.*, 7(2), 377-384 (1988).
Breda et al., "Therapeutic hemoglobin levels after gene transfer in beta-thalassemia mice and in hematopoietic cells of beta-thalassemia and sickle cells disease patients," *PLoS One*, 7(3), 16 pp. (2012).
Burt et al., "Clinical applications of blood-derived and marrow-derived stem cells for nonmalignant diseases," *JAMA*, 299 (8), 925-936 (2008)
Chandrakasan et al., "Gene therapy for hemoglobinopathies: the state ofthe field and the future,"*Hematol. Oncol. Clin. North Am.*, 28(2), 199-216 (2014), Author Manuscript.
Csaszar et al., "Rapid expansion of human hematopoietic stem cells by automated control of inhibitory feedback signaling," *Cell Stem Cell*, 10(2), 218-229 (2012).
Deboer et al., "The human beta-globin promoter; nuclear protein factors and erythroid sgecific induction of transcription," *EMBO J.*, 7 (13), 4203-4212 (1988).
Donello et al., "Woodchuck hepatitis virus contains a tripartite posttranscriptional regulatory element," *J. Virol.*, 72(6), 5085-5092 (1998).
Fernandes et al., "The HIV-1 Rev response element: an RNA scaffold that directs the cooperative assembly of a homo-oligomeric ribonucleoprotein complex," *RNA Biol.*, 9(1), 6-11 (2012).
Forrester et al., "A developmentally stable chromatin structure in the human beta-qlobin gene cluster," Proc. Natl. Acad. Sci. USA, 83 (5), 1359-1363 (1986).
Frisch et al., "Hematopoietic stem cell cultures and assays," *Methods Mol. Biol.*, 1130, 315-324 (2014), Author Manuscript.
GenBank Accession No. BC029387.1, 2 pages.
GenBank Accession No. M91036.1, 5 pages.
Hanawa et al., "Comparison of various envelope proteins for their ability to pseudotype lentiviral vectors and transduce primitive hematopoietic cells from human blood," *Mol. Ther.*, 5 (3), 242-251 (2002).
Hanawa et al., "Extended beta-globin locus control region elements promote consistent therapeutic expression of a gamma-globin lentiviral vector in murine beta-thalassemia," *Blood*, 104 (8), 2281-2290 (2004).

(Continued)

*Primary Examiner* — Maria Marvich
(74) *Attorney, Agent, or Firm* — Leydig, Voit & Mayer, Ltd.

(57) ABSTRACT

The invention is directed to a more efficient lentiviral vector comprising a nucleic acid sequence encoding a human β-globin protein or a human γ-globin protein, which is oriented from 5' to 3' relative to the lentiviral genome. The invention also provides a composition and method utilizing the lentiviral vector.

20 Claims, 11 Drawing Sheets

(56) References Cited

OTHER PUBLICATIONS

Hardison et al., "Locus control regions of mammalian beta-globin gene clusters: combining phylogenetic analyses and experimental results to gain functional insights," *Gene*, 205 (1-2), 73-94 (1997).
Hargrove et al., "Globin lentiviral vector insertions can perturb the expression of endogenous genes in beta-thalassemic hematopoietic cells," *Molecular Therapy*, 16 (3), 525-533 (2008).
Jackson et al., "Beta-globin locus control region HS2 and HS3 interact structurally and functionally," *Nucleic Acids Res.*, 31 (4), 1180-1190 (2003).
Kutner et al., "Production, concentration and titration of pseudotyped HIV-1-based lentiviral vectors," *Nat. Protoc.*, 4 (4), 495-505 (2009).
Lanzkron et al., "Systematic review: Hydroxyurea for the treatment of adults with sickle cell disease," *Ann. Intern. Med.*, 148 (12), 939-955 (2008), Author Manuscript.
Levasseur et al., "A recombinant human hemoglobin with anti-sickling properties greater than fetal hemoglobin," *J. Biol. Chem.*, 279 (26), 27518-27524 (2004).
Levasseur et al., "Correction of a mouse model of sickle cell disease: lentiviral/antisickling beta-globin gene transduction of unmobilized, purified hematopoietic stem cells," *Blood*, 102 (13), 4312-4319 (2003).
Levings et al., "The human beta-globin locus control region," *Eur. J. Biochem*, 269 (6), 1589-1599 (2002).
Li et al., "Locus control regions," *Blood*, 100 (9), 3077-3086 (2002).
Li et al., "Locus control regions: coming of age at a decade plus," *Trends Genet.*, 15 (10), 403-408 (1999).
Madlambayan et al., "Clinically relevant expansion of hematopoietic stem cells with conserved function in a single-use, closed-system bioprocess," *Biol. Blood Marrow Transplant.*, 12 (10), 1020-1030 (2006).
Matrai et al., "Recent advances in lentiviral vector development and applications," *Mol. Ther.*, 18 (3), 477-490 (2010).
May et al., "Therapeutic haemoglobin synthesis in beta-thalassaemic mice expressing lentivirus-encoded human beta-globin," *Nature*, 406 (6791), 82-86 (2000).
Migliaccio et al., "In vitro mass production of human erythroid cells from the blood of normal donors and of thalassemic patients," *Blood Cells Mol. Dis.*, 28 (2), 169-180 (2002).
Miller et al., "Design of retrovirus vectors for transfer and expression of the human beta-globin gene," *J. Virol.*, 62 (11), 4337-4345 (1988).
Naldini et al., "In vivo gene delivery and stable transduction of nondividing cells by a lentiviral vector," *Science*, 272 (5259), 263-267 (1996).
Ng et al., "Isolation of human and mouse hematopoietic stem cells," *Methods Mol. Biol.*, 506, 13-21 (2009).
Oh et al., "Expression of an anti-sickling beta-globin in human erythroblasts derived from retrovirally transduced primitive normal and sickle cell disease hematopoietic cells," *Exp. Hematol.*, 32 (5), 461-469 (2004).
Papanikolaou et al., "The new self-inactivating lentiviral vector for thalassemia gene therapy combining two HPFH activating elements corrects human thalassemic hematopoietic stem cells," *Hum. Gene Ther.*, 23 (1), 15-31 (2012).
Pawliuk et al., "Correction of sickle cell disease in transgenic mouse models by gene therapy," *Science*, 294 (5550), 2368-2371 (2001).
Persons et al., "The degree of phenotypic correction of murine beta-thalassemia intermedia following lentiviral-mediated transfer of a human gamma-globin gene is influenced by chromosomal position effects and vector copy number," *Blood*, 101 (6), 2175-2183 (2003).
Pestina et al., "Correction of murine sickle cell disease using gamma-globin lentiviral vectors to mediate high-level expression of fetal hemoglobin," *Mol. Ther.*, 17 (2), 245-252 (2009).
Puthenveetil et al., "Successful correction of the human beta-thalassemia major phenotype using a lentiviral vector," *Blood*, 104 (12), 3445-3453 (2004).
Reik et al., "The locus control region is necessary for gene expression in the human beta-globin locus but not the maintenance of an open chromatin structure in erythroid cells," *Mol. Cell. Biol.*, 18 (10), 5992-6000 (1998).
Romero et al., "beta-globin gene transfer to human bone marrow for sickle cell disease," *J. Clin. Invest.*, 123 (8), 3317-3330 (2013).
Schambach et al., "Biosafety features of lentiviral vectors," *Hum. Gene Ther.*, 24 (2), 132-142 (2013).
Slightom et al., "Human fetal G gamma- and a gamma-globin genes: complete nucleotide sequences suggest that Dna can be exchanged between these duplicated genes," *Cell*, 21 (3), 627-638 (1980).
Steinberg et al., "Genetic modifiers of sickle cell disease," *Am. J. Hematol.*, 87 (8), 795-803 (2012), Author Manuscript.
Taniguchi et al., "Rev protein specifies the viral Rna export pathway by suppressing TAP/NXF1 recruitment," *Nucleic Acids Research*, 42(10), 6645-6658 (2014).
Tuan et al., "The 'beta-like-globin' gene domain in human erythroid cells," *Proc. Natl. Acad. Sci. USA*, 82 (19), 6384-6388 (1985).
Uchida et al., "Chicken HS4 insulators have minimal barrier function among progeny of human hematopoietic cells transduced with an HIV1-based lentiviral vector," *Mol. Ther.*, 19 (1), 133-139 (2011).
Uchida et al., "Development of a human immunodeficiency virus type 1-based lentiviral vector that allows efficient transduction of both human and rhesus blood cells," *J. Virol.*, 83 (19), 9854-9862 (2009).
Uchida et al., "Integration-specific in vitro evaluation of lentivirally transduced rhesus CD34+ cells correlates with in vivo vector copy number," *Mol. Ther. Nucleic Acids*, 2, 8 pp. (2013).
Uchida et al., "Leukemogenesis of b2a2-type p210 BCR/ABL in a bone marrow transplantation mouse model using a lentiviral vector," *J. Nippon Med. Sch.*, 76 (3), 134-147 (2009).
Uchida et al., "Optimal conditions for lentiviral transduction of engrafting human CD34+ cells," *Gene Ther.*, 18 (11), 1078-1086 (2011).
Vigna et al., "Lentiviral vectors: excellent tools for experimental gene transfer and promising candidates for gene therapy," *J. Gene Med.*, 2 (5), 308-316 (2000).
Weissman et al., "The origins of the identification and isolation of hematopoietic stem cells, and their capability to induce donor-specific transplantation tolerance and treat autoimmune diseases," *Blood*, 112 (9), 3543-3553 (2008).
Wilber et al., "Therapeutic levels of fetal hemoglobin in erythroid progeny of beta-thalassemic CD34+ cells after lentiviral vector-mediated gene transfer," *Blood*, 117 (10), 2817-2826 (2011).
Wognum et al., "Identification and isolation of hematopoietic stem cells," *Arch. Med. Res.*, 34 (6), 461-475 (2003).
Woods et al., "Brief report: efficient generation of hematopoietic precursors and progenitors from human pluripotent stem cell lines," *Stem Cells*, 29 (7), 1158-1164 (2011).
Zhao et al., "Amelioration of murine beta-thalassemia through drug selection of hematopoietic stem cells transduced with a lentiviral vector encoding both gamma-globin and the MGMT drug-resistance gene," *Blood*, 113 (23), 5747-5756 (2009).
Zufferey et al., "Woodchuck hepatitis virus posttranscriptional regulatory element enhances expression of transgenes delivered by retroviral vectors," *J. Virol.*, 73 (4), 2886-2892 (1999).
Ronen et al., "Distribution of Lentiviral Vector Integration Sites in Mice Following Therapeutic Gene Transfer to Treat β-thalassemia," *Molecular Therapy*, vol. 19 No. 7, pp. 1273-1286 (Jul. 2011).

* cited by examiner

LENTIVIRAL VECTOR FOR TREATING HEMOGLOBIN DISORDERS

CROSS-REFERENCE TO RELATED APPLICATIONS

This patent application is a divisional application of U.S. patent application Ser. No. 15/510,014, filed Mar. 9, 2017, now U.S. Pat. No. 10,543,257, which is a U.S. National Phase of International Patent Application No. PCT/US2015/045358, filed Aug. 14, 2015, which claims the benefit of U.S. Provisional Patent Application No. 62/048,881, filed Sep. 11, 2014, each of which is incorporated herein by reference in its entirety.

STATEMENT REGARDING FEDERALLY SPONSORED RESEARCH AND DEVELOPMENT

This invention was made with Government support under project number Z01 HL006008 by the National Institutes of Health, National Heart, Lung, and Blood Institute. The Government has certain rights in the invention.

BACKGROUND OF THE INVENTION

Sickle cell disease (SCD) (also known as sickle cell anemia (SCA) and drepanocytosis) and β-thalassemia are inherited blood disorders that are caused by mutations in the β-globin gene (HBB). Sickle cell disease is characterized by atypical hemoglobin molecules which can distort red blood cells into a sickle, or crescent, shape and lead to anemia. β-thalassemia is characterized by reduced amounts of hemoglobin and fewer circulating red blood cells than normal, which results in mild or severe anemia.

Sickle cell disease is the most common inherited single-gene disorder. One out of every 12 African-Americans carries the sickle cell allele, and one out of every 500 African-American children is born with sickle cell disease. Annually there are over 332,000 conceptions or births affected by sickle cell disease worldwide. Approximately 56,000 people are affected with a major thalassemia (α or β) worldwide (see, e.g., Piel, F. B., *Nat Commun.*, 1(104): 1-7 (2010)).

Sickle cell disease has no widely available cure. Currently, allogeneic hematopoietic stem cell (HSC) transplantation, in which normal HSCs are harvested from a suitable donor and transplanted into a sickle cell disease patient, can cure sickle cell disease patients. However, suitable donors (often siblings) are found in only about 10% of sickle cell disease patients, and there is a significant risk of rejection and graft-versus host disease (GVHD). Blood and marrow stem cell transplants may offer a cure for a small number of people. Treatments for thalassemias depend on the type and severity of the disorder, but there is no general cure. Like sickle cell disease, allogeneic HSC transplantation is effective in a small percentage of patients.

Thus, there is a need for alternative treatments for diseases associated with mutations in the β-globin gene, such as sickle cell disease and thalassemias. The invention provides such a treatment.

BRIEF SUMMARY OF THE INVENTION

The invention provides a lentiviral vector comprising a nucleic acid sequence encoding a human β-globin protein and operably linked to a native human β-globin gene promoter, wherein (i) the nucleic acid sequence is oriented from 5' to 3' relative to the lentiviral genome and (ii) the endogenous Rev response element (RRE) of the lentiviral genome is deleted and inserted into intron 2 of the nucleic acid sequence encoding the human β-globin protein.

The invention provides a lentiviral vector comprising a nucleic acid sequence encoding a human γ-globin protein operably linked to a native human β-globin gene promoter and a woodchuck hepatitis virus post-transcriptional regulatory element (WPRE), wherein the nucleic acid sequence is oriented from 5' to 3' relative to the lentiviral genome.

The invention also provides a composition and method utilizing the aforementioned lentiviral vectors.

BRIEF DESCRIPTION OF THE SEVERAL VIEWS OF THE DRAWING(S)

FIG. 1 is an image depicting the results of hemoglobin electrophoresis illustrating hemoglobin A expression in β-thalassemia erythroid cells transduced with different β-globin-encoding lentiviral vector constructs. "HbA" denotes hemoglobin A, "HbF" denotes hemoglobin F, and "eHb" denotes embryonic hemoglobin. The "Forward-oriented BG gene vector" is the inventive lentiviral vector comprising a human β-globin-encoding nucleic acid sequence oriented from 5' to 3' relative to the lentiviral genome and the endogenous RRE inserted into intron 2 of β-globin gene. Hemoglobin A expression from the "Forward-oriented BG gene vector" was compared to hemoglobin A expression from a lentiviral vector comprising a human β-globin gene expression cassette oriented from 3' to 5' with respect to the lentiviral genome ("Reverse-oriented BG gene vector"), a lentiviral vector containing a forward-oriented β-globin gene lacking introns ("Forward-oriented BG cDNA vector (without introns)") and control cells that were not transduced with lentiviral vector.

Figure 4:
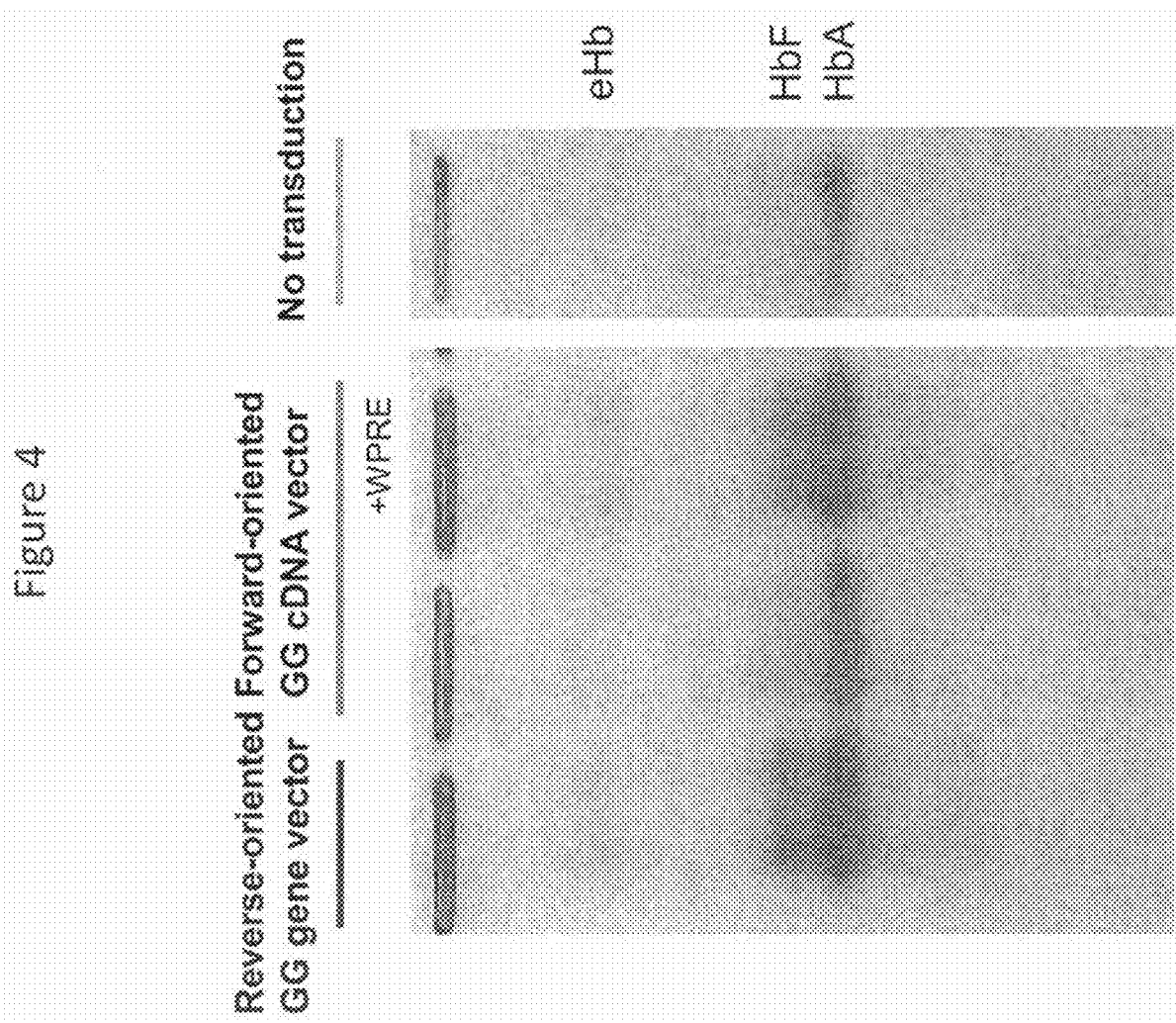

FIG. 4 is an image depicting the results of hemoglobin electrophoresis illustrating hemoglobin F expression in healthy erythroid cells transduced with different γ-globin-encoding lentiviral vector constructs. "HbA" denotes hemoglobin A, "HbF" denotes hemoglobin F, and "eHb" denotes embryonic hemoglobin. The "Forward-oriented GG cDNA vector" is the inventive lentiviral vector comprising a human γ-globin-encoding nucleic acid sequence oriented from 5' to 3' relative to the lentiviral genome. Hemoglobin F expression from the "Forward-oriented GG cDNA vector" was compared to hemoglobin F expression from a lentiviral vector comprising a human γ-globin gene expression cassette oriented from 3' to 5' with respect to the lentiviral genome ("Reverse-oriented GG gene vector") and control cells that were not transduced with lentiviral vector.

Figure 5A:
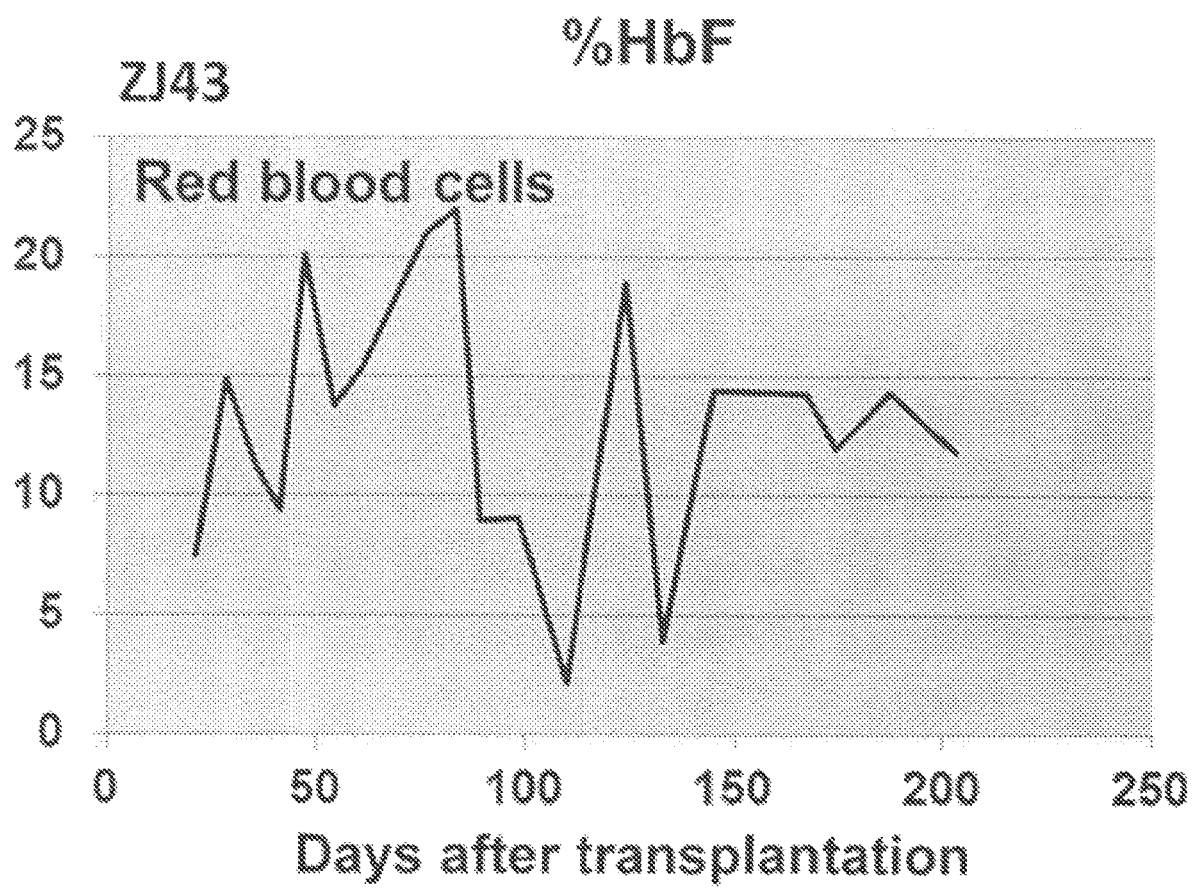

FIG. 5A is a graph depicting experimental results illustrating hemoglobin F expression in a rhesus monkey (ZJ43) transplanted with rhesus CD34+ cells transduced with the inventive lentiviral vector expressing γ-globin.

Figure 5B:
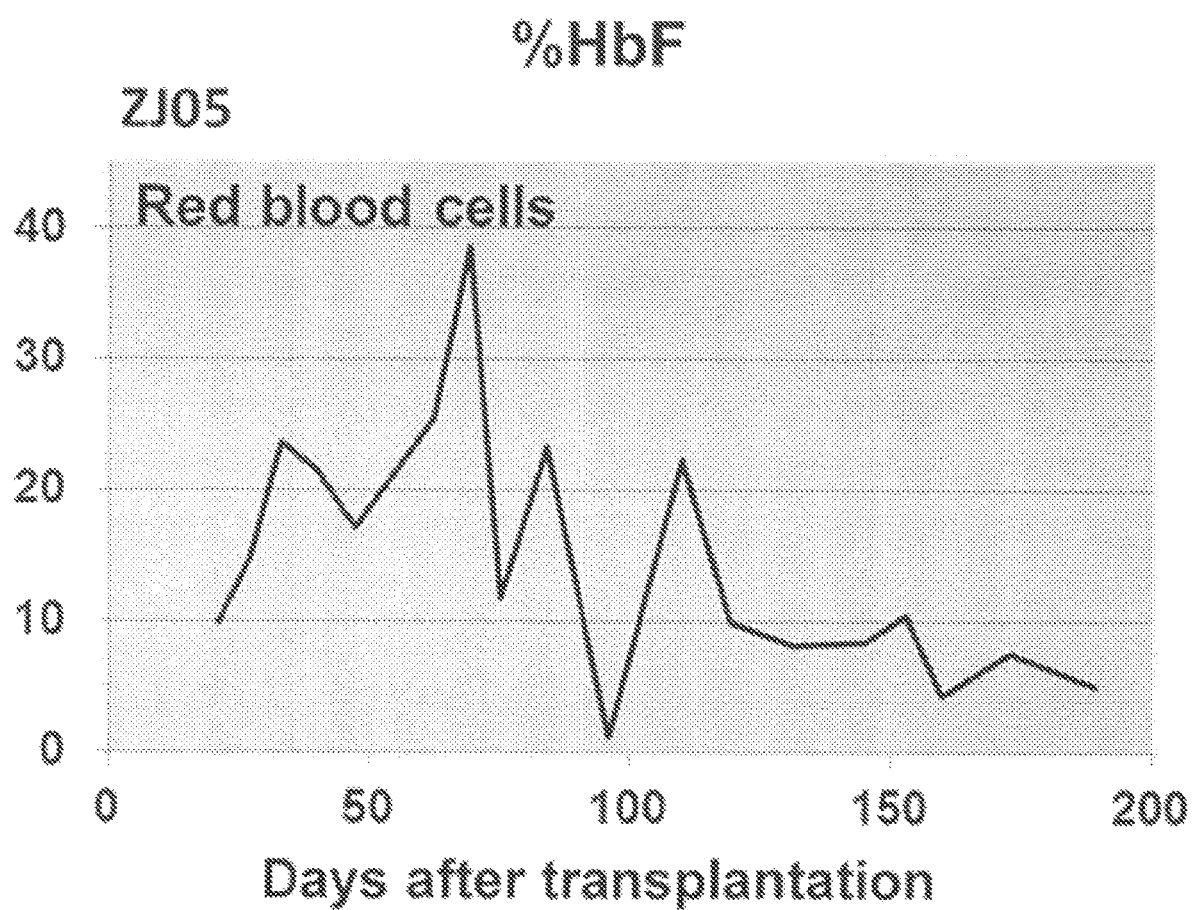

FIG. 5B is a graph depicting experimental results illustrating hemoglobin F expression in a rhesus monkey (ZJ05) transplanted with rhesus CD34+ cells transduced with the inventive lentiviral vector expressing γ-globin.

Figure 5C:
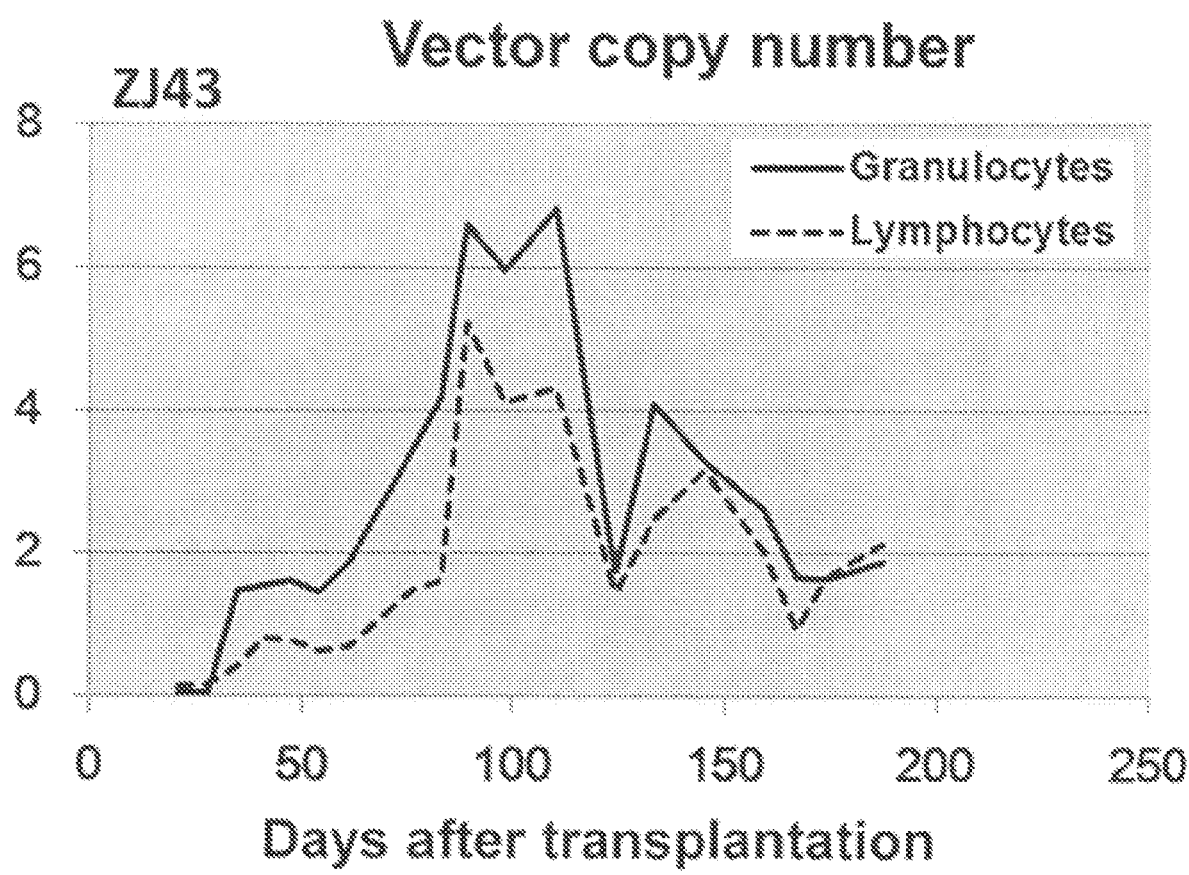

FIG. 5C is a graph depicting experimental results illustrating lentiviral vector copy number in a rhesus monkey (ZJ43) transplanted with rhesus CD34+ cells transduced with the inventive lentiviral vector expressing γ-globin.

Figure 5D:
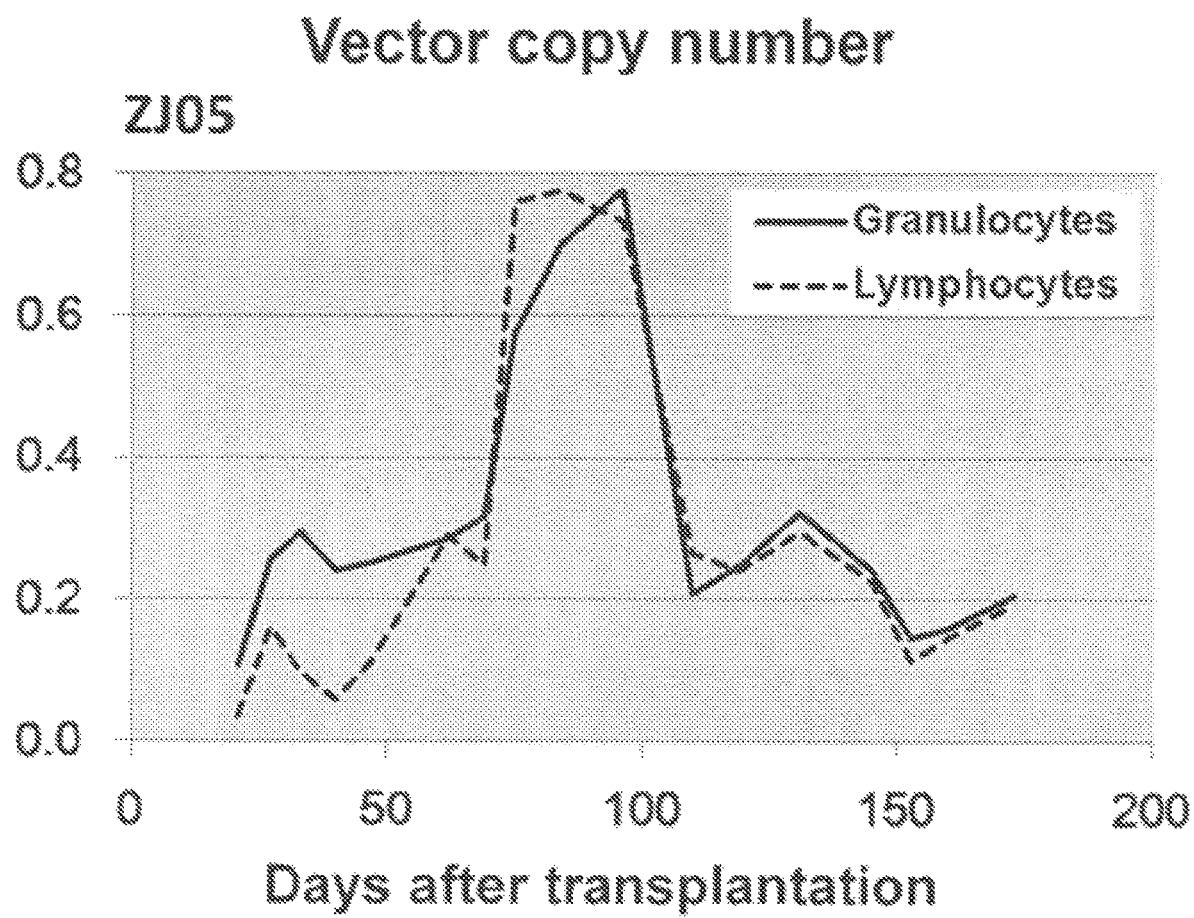

FIG. 5D is a graph depicting experimental results illustrating lentiviral vector copy number in a rhesus monkey (ZJ05) transplanted with rhesus CD34+ cells transduced with the inventive lentiviral vector expressing γ-globin.

DETAILED DESCRIPTION OF THE INVENTION

The invention is predicated, at least in part, on the discovery that a lentiviral vector encoding the β-globin gene or the γ-globin gene in a forward orientation can be grown at higher titers and induce production of human hemoglobins A and F, respectively, in rhesus macaques via hematopoietic stem cell transplantation with more efficient transduction than currently available lentiviral vectors.

Lentiviruses are a subclass of Retroviruses. Lentiviruses resemble γ-retroviruses (γ-RV) in their ability to stably integrate into the target cell genome, resulting in persistent expression of the gene of interest. However, in contrast to γ-retroviruses, lentiviruses also can transduce nondividing cells, which has led to their wide use as gene transfer vectors. The lentivirus genome is monopartite, linear, dimeric, positive-strand single-stranded RNA ("ssRNA(+)") of 9.75 kb, with a 5'-cap and a 3'poly-A tail. The lentiviral genome is flanked by the 5' and 3' long terminal repeat (LTR) sequences which have promoter/enhancer activity and are essential for the correct expression of the full-length lentiviral vector transcript. The LTRs also have an important role in reverse transcription and integration of the vector into the target cell genome. Upon viral entry into a cell, the RNA genome is reverse-transcribed into double-stranded DNA, which is then inserted into the genome at a random position by the viral integrase enzyme. The lentivirus, now called a provirus, remains in the genome and is passed on to the progeny of the cell when it divides. Species of lentivirus include, for example, human immunodeficiency virus 1 (HIV-1), human immunodeficiency virus 2 (HIV-2), simian immunodeficiency virus (SIV), bovine immunodeficiency virus (BIV), and feline immunodeficiency virus (FIV). The lentiviral vector of the invention can be based on any lentivirus species. Preferably, the lentiviral vector is based on a human immunodeficiency virus (e.g., HIV-1 or HIV-2), most preferably HIV-1.

Lentiviral vectors typically are generated by trans-complementation in packaging cells that are co-transfected with a plasmid containing the vector genome and the packaging constructs that encode only the proteins essential for lentiviral assembly and function. A self-inactivating (SIN) lentiviral vector can be generated by abolishing the intrinsic promoter/enhancer activity of the HIV-1 LTR, which reduces the likelihood of aberrant expression of cellular coding sequences located adjacent to the vector integration site (see, e.g., Vigna et al., *J. Gene Med.*, 2: 308-316 (2000); Naldini et al., *Science*, 272: 263-267 (1996); and Mátrai et al., *Molecular Therapy*, 18(3): 477-490 (2010)). The most common procedure to generate lentiviral vectors is to co-transfect cell lines (e.g., 293T human embryonic kidney cells) with a lentiviral vector plasmid and three packaging constructs encoding the viral Gag-Pol, Rev-Tat, and envelope (Env) proteins.

In one embodiment, the lentiviral vector comprises a nucleic acid sequence encoding a human β-globin protein or a human γ-globin protein and operably linked to a native human β-globin gene promoter. The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The human β-globin gene locus includes five genes arranged in a linear array on chromosome 11, and is responsible for the creation of the beta (β) parts (i.e., approximately half) of the oxygen transport protein hemoglobin. The human β-globin gene locus contains epsilon (ε), gamma-A (Aγ), gamma-G (Gγ), delta (δ), and β-globin. Expression of all of these genes is controlled by the single locus control region (LCR), and the genes are differentially expressed throughout development (see, e.g., Levings and Bungert, *Eur. J. Biochem.*, 269: 1589-1599 (2002)). During normal human development, the ε-globin gene is expressed in the first trimester in erythroid cells derived from yolk sac hematopoiesis. The γ-globin genes (HBG1 and HBG2) are normally expressed in the fetal liver, spleen, and bone marrow. Two gamma chains together with two alpha chains constitute fetal hemoglobin (HbF), which is normally replaced by adult hemoglobin (HbA) at birth. In some beta-thalassemias and related conditions, gamma chain production continues into adulthood. The two types of gamma chains differ at residue 136 where glycine is found in the Gγ product (HBG2) and alanine is found in the Aγ product (HBG1). The former is predominant at birth. The adult β-globin gene is expressed around birth predominantly in cells derived from bone marrow hematopoiesis.

The β-globin genes are arranged in the following order from 5' to 3': ε-Gγ-Aγ-δ-β. The coding sequences of all human globin genes are separated by two introns into three exons. The first exon has a short 5' untranslated region followed by a coding region. All of the second exon codes for protein, while the third exon begins with coding sequences and ends with a 3' untranslated region. The second intron ("intron 2") of the human β-globin gene is required for high-levels of β-globin expression in gene transfer vectors (see, e.g., Miller et al., *J. Virol.*, 62(11):

4337-4345 (1998)). Desirably, the nucleic acid sequence encodes a human β-globin protein that is resistant to sickling (also referred to as an "anti-sickling" β-globin protein). Recombinant nucleic acid sequences encoding anti-sickling β-globin protein have been generated and can be used in the inventive lentiviral vector (see, e.g., Romero et al., *J. Clin. Invest.,* 123(8): 3317-3330 (2013); Oh et al., *Exp. Hematol.,* 32(5): 461-469 (2004); Levasseur et al., *J. Biol. Chem.,* 279: 27518-27524 (2004); and U.S. Pat. No. 5,861,488). In addition, a human γ-globin resistant to sickling (Persons et al., *Blood,* 101(6): 2175-83 (2003); and Hargrove et al., *Mol. Ther.,* 16(3): 525-33 (2008)) can be used in the inventive lentiviral vector. Preferably, the nucleic acid sequence encodes a wild-type human β-globin protein or a wild-type human γ-globin protein. The wild-type nucleic acid sequence of the human β-globin gene locus is publicly available via the National Center for Biotechnology Information (NCBI) (NCBI Reference Sequence: NG_000007.3). The wild-type nucleic acid sequences of the human A-γ-globin gene (HBG1) and G-γ-globin gene (HBG2) also are publicly available via the NCBI (GenBank Accession Nos. M91036.1 and BC029387.1, respectively), and are disclosed in, e.g., Slighthom et al., *Cell,* 21(3): 627-38 (1980).

One of ordinary skill in the art would appreciate that, to achieve maximum therapeutic benefit, the inventive lentiviral vector must be capable of expressing high levels of human β-globin or human γ-globin in a mammal, preferably a human. Thus, in one embodiment, the nucleic acid sequence encoding a human β-globin protein or human γ-globin protein is codon-optimized. A nucleic acid sequence can be "codon-optimized" using an algorithm to design a nucleic sequence that is expressed at optimal levels in host cells. Such an algorithm typically takes into account various factors associated with gene expression, such as, for example, GC content, ribosomal binding sites, splice sites, repeats, and secondary structures (see, e.g., Puigbò et al., *Nucleic Acids Res.,* 35: W126-31 (2007)). Codon optimization allows for improvement of messenger RNA stability, often resulting in higher protein production.

The human β-globin protein (also referred to herein as HBB or β-globin) is 146 amino acids long and has a molecular weight of 15,867 Da. β-globin, together with the human α-globin protein, make up hemoglobin A, which is the most common form of hemoglobin in adult humans. Hemoglobin A (HbA) comprises over 97% of the total red blood cell hemoglobin, and consists of two α-globin chains and two β-globin chains.

More than 1000 natural variants of the β-globin gene have been identified. A single point mutation in the β-globin (HBB) gene leads to sickle cell disease. This mutation results in the production of an abnormal version of β-globin called hemoglobin S (HbS). In sickle cell disease, hemoglobin S replaces both β-globin subunits in hemoglobin. The point mutation results in replacement of a GAG codon with GTG, which substitutes a glutamic acid residue with a valine residue at position 6 in the β-globin protein. Replacing glutamic acid with valine causes the abnormal hemoglobin S subunits to stick together and form long, rigid molecules. The rigid hemoglobin S molecules bend red blood cells into a sickle, or crescent, shape. The sickle-shaped cells die prematurely, which can lead to sickle cell disease. The sickle-shaped cells also can block small blood vessels, causing pain and organ damage.

Thalassemia is an autosomal recessive disorder that is caused by mutations in the α-globin gene (α-thalassemia), the β-globin gene (β-thalassemia), or less commonly, the δ-globin gene (δ-thalassemia). Both α- and β-thalassemia can occur in two forms: thalassemia major or thalassemia minor. Inheritance of two mutant globin genes, one from each parent, results in thalassemia major. Inheritance of only one mutant globin gene from one parent results in thalassemia minor. Humans with thalassemia minor are carriers of the disease and typically do not exhibit disease symptoms.

More than 250 mutations in the β-globin gene have been found to cause β-thalassemia. Most of the mutations involve a change in a single nucleotide within or near the β-globin gene. Other mutations insert or delete a small number of nucleotides in the HBB gene. β-globin gene mutations that decrease β-globin production result in a type of thalassemia called β-plus (B+) thalassemia. Mutations that prevent cells from producing any β-globin result in β-zero (B0) thalassemia. Without proper amounts of β-globin, sufficient hemoglobin cannot be formed. A lack of hemoglobin disrupts the normal development of red blood cells.

Mutations in the β-globin gene can cause other abnormalities in β-globin, leading to other types of sickle cell disease or thalassemias. Two of the most common variants are hemoglobin C and hemoglobin E. Hemoglobin C (HbC), caused by a Glu6Lys mutation in β-globin, is more common in people of West African descent than in other populations. In hemoglobin SC (HbSC) disease, the β-globin subunits are replaced by hemoglobin S and hemoglobin C. Hemoglobin C disease occurs when both β-globin subunits are replaced with hemoglobin C subunits, and is a mild condition characterized by chronic anemia in which the red blood cells are broken down prematurely.

Hemoglobin E (HbE), caused by a Glu26Lys mutation in β-globin, is a variant of hemoglobin most commonly found in the Southeast Asian population. In some cases, the hemoglobin E mutation can be present with hemoglobin S, which may lead to more severe signs and symptoms associated with sickle cell disease, such as episodes of pain, anemia, and abnormal spleen function. Hemoglobin E disease occurs when both β-globin subunits are replaced with hemoglobin E subunits. The mutations that produce hemoglobin E and β-thalassemia also can occur together, which may produce symptoms ranging from mild anemia to severe thalassemia major.

Other conditions, known as hemoglobin sickle-β-thalassemias (HbS-βThal), are caused when mutations that produce hemoglobin S and β-thalassemia occur together. The symptoms of hemoglobin S-β-thalassemias are usually more severe than those of hemoglobin SC disease, and may include severe pain and organ damage.

As discussed above, while adult hemoglobin is composed of two α (alpha) and two β (beta) subunits, fetal hemoglobin (HBF) is composed of two a subunits and two γ (gamma) subunits, and is commonly denoted α2γ2. HBF typically persists in newborns until it is replaced completely with HBA at about 6 months of age. In some beta-thalassemias and related conditions, however, gamma chain production continues into adulthood. Fetal hemoglobin has been shown to protect against many of the complications of sickle-cell anemia (see, e.g., Steinberg, M. H. and Sebastiani P., *Am. J. Hematol.,* 87: 795-803 (2012)). In adults, fetal hemoglobin production can be reactivated pharmacologically, which is useful in the treatment of diseases such as sickle-cell disease (see, e.g., Lanzkron et al., *Annals of Internal Med.,* 148(12): 939-955 (2008)).

The nucleic acid sequence encoding a human β-globin protein or a γ-globin protein is operably linked to a native human β-globin gene promoter. By "native" is meant that the promoter is the same promoter that controls expression of the human β-globin gene cluster in nature, and is located in the same position relative to the human β-globin gene as found in nature, i.e., 5' of the human β-globin gene cluster (see, e.g., Antoniou et al., *The EMBO Journal*, 7(2): 377-384 (1988); and deBoer et al., *The EMBO Journal*, 7(13): 4203-4212 (1988)). Thus, in one embodiment of the invention, the human β-globin gene is not dissociated from its endogenous β-globin promoter during construction of the inventive lentiviral vector. Alternatively, the human β-globin gene can be dissociated from its endogenous β-globin promoter during construction of the inventive lentiviral vector (e.g., present on separate nucleic acid molecules), but operatively linked in the lentiviral vector such that the position of the β-globin promoter relative to the β-globin gene is identical to its position in nature. The nucleic acid sequence of the native human β-globin gene promoter is disclosed in, for example, Antoniou et al., supra, and deBoer et al., supra.

The nucleic acid sequence encoding a human γ-globin protein also is operably linked to a woodchuck hepatitis virus post-transcriptional regulatory element (WPRE). The WPRE is a tripartite cis-acting RNA element that is required for the cytoplasmic accumulation of woodchuck hepatitis virus (WHV) surface RNAs which has been shown to enhance transgene expression from retroviral vectors and improve their performance (see, e.g., Donello et al., *J. Virol.*, 72(6): 5085-5092 (1998); and Zufferey et al., *J. Virol.*, 73(4): 2886-2892 (1999)). The WPRE is two to three times more active than the bipartite post-transcriptional regulatory element of the closely related hepatitis B virus (HBVPRE) (Donello et al., supra).

The nucleic acid sequence encoding a human β-globin protein or γ-globin protein and operably linked to a native human β-globin gene promoter is oriented in the lentiviral vector from 5' to 3' relative to the lentiviral genome. To date, lentiviral vectors encoding β-globin or γ-globin developed for the treatment of sickle cell disease or thalassemia include the β-globin or γ-globin gene in reverse orientation with respect to the lentiviral genome (see, e.g., May et al., *Nature*, 406, 82-86 (6 Jul. 2000); Pawliuk et al., *Science*, 294(5550): 2368-2371 (2001); Persons et al., *Blood*, 101(6): 2175-83 (2003); Hanawa et al., *Blood*, 104(8): 2281-90 (2004); Levasseur et al., *Blood*, 102(13): 4312-4319 (2003); Pestina et al., *Mol. Ther.*, 17(2): 245-252 (2009); and Puthenveetil et al., *Blood*, 104(12): 3445-3453 (2004)). In other words, in these lentiviral vectors the β-globin gene or the γ-globin gene is oriented from 3' to 5' relative to the lentiviral genome. Reversing the orientation of the β-globin gene expression cassette prevents loss of intron 2 of the β-globin gene during splicing, which is necessary for high levels off β-globin gene expression (see Miller et al., supra). Such reverse-oriented lentiviral vectors, however, cannot be produced in high titers and exhibit low gene transfer efficiency to human blood cells.

In contrast, in the inventive β-globin-expressing lentiviral vector loss of intron 2 is prevented by modification of the endogenous Rev response element (RRE) of the lentiviral genome. In this respect, the endogenous RRE of the lentiviral genome is deleted and inserted into intron 2 of the human β-globin gene. The RRE is a 350 nucleotide, highly structured, cis-acting RNA element essential for viral replication. It is located in the Env coding region of the viral genome and is extremely well conserved. The RRE is present on all partially spliced and unspliced viral mRNA transcripts, and serves as an RNA framework onto which multiple molecules of the viral protein Rev assemble. The Rev-RRE oligomeric complex mediates the export of these mRNAs messages from the nucleus to the cytoplasm, where they are translated to produce essential viral proteins and/or packaged as genomes for new virions (see, e.g., Fernandes et al., *RNA Biol.*, 9(1): 6-11 (2012)). Insertion of the endogenous RRE element into the intron 2 of the human β-globin gene allows for positive selection of the inventive forward-oriented lentiviral vector. The endogenous RRE can be deleted from the lentiviral genome and inserted into intron 2 of the human β-globin gene using routine recombinant DNA techniques known in the art.

In addition to the human β-globin gene or γ-globin gene, β-globin promoter, and RRE, the inventive lentiviral vector desirably comprises other elements necessary for viral replication and packaging. Such elements include long terminal repeats (LTRs) (e.g., self-inactivating LTRs (SIN-LTRs)), a packaging signal, a locus control region (LCR), and a 3' untranslated region. The LTRs, including SIN-LTRs, are identical sequences of DNA that flank the ends of the retroviral genome and are necessary for integration of the double-stranded viral genome into the host chromosome. The packaging signal (also referred to as a "packaging sequence" or "Psi (Ψ)-sequence") is located in the 5' LTR and is necessary for packaging viral RNA into virus capsids. A locus control region (LCR) is a nucleic acid sequence that is operationally defined by its ability to enhance the expression of linked genes to physiological levels in a tissue-specific and copy number-dependent manner at ectopic chromatin sites. LCRs have been identified in a large number of mammalian genes, including the human β-globin locus (see, e.g., Li et al., *Blood*, 100(9): 3077-3086 (2002); and Li et al., *Trends Genet.*, 15(10): 403-8 (1999)). The β-globin LCR is a 5 kb regulatory element 10-60 kb upstream of the globin structural genes. The LCR encompasses six highly conserved subdomains, HS1, HS2, HS3, HS4, HS5, and 3'HS1, which were originally identified as DNase I hypersensitive sites (HSs) (see, e.g., Reik et al., *Mol. Cell. Biol.*, 18: 5992-6000 (1998); Hardison et al., Gene, 205, 73-94 (1997); Forrester et al., *Proc. Natl Acad. Sci. USA*, 83: 1359-1363 (1986); Tuan et al., *Proc. Natl Acad. Sci. USA*, 82: 6384-6388 (1985); and Jackson et al., *Nucleic Acids Res.*, 31(4): 1180-1190 (2003)). The 3' untranslated region (3'UTR) is a sequence transcribed into RNA but not translated into protein, and typically contains regulatory regions that influence post-transcriptional gene expression.

The foregoing elements of the lentiviral vector can be arranged in any order, so long as the lentiviral vector can be produced at high titers, can efficiently transduce host cells, and can express the human β-globin or γ-globin gene at therapeutically effective levels. In a preferred embodiment, the inventive β-globin-expressing lentiviral vector comprises the following elements in sequence from 5' to 3' relative to the lentiviral genome: (a) a first long terminal repeat (LTR), (b) a packaging signal, (c) a locus control region (LCR), (d) a native human β-globin gene promoter, (e) the nucleic acid sequence encoding a human β-globin, (f) a 3' untranslated region (UTR), and (g) a second LTR. In another preferred embodiment, the inventive γ-globin-expressing lentiviral vector comprises the following elements in sequence from 5' to 3' relative to the lentiviral genome: (a) a first long terminal repeat (LTR) (b) a packaging signal, (c) a locus control region (LCR), (d) a native human β-globin gene promoter (e) a nucleic acid sequence encoding a human γ-globin protein, (f) a 3' untranslated region (UTR), (g) a woodchuck hepatitis virus post-transcriptional regulatory element (WPRE), and (h) a second LTR.

Methods for generating lentiviral vectors are well-known in the art, and the inventive lentiviral vector can be constructed using any suitable such method. Lentiviral vectors typically are produced by co-transfecting 293T human embryonic kidney cells with several different plasmid constructs, which separately contain the lentiviral cis-acting sequences and trans-acting factors that are required for viral particle production, infection, and integration. Lentiviral vector production systems typically include four plasmids. The transfer vector contains the transgene be delivered in a lentiviral backbone containing all of the cis-acting sequences required for genomic RNA production and packaging. Three additional provide the trans-acting factors required for packaging, namely Gag-Pol, Rev-Tat, and the envelope protein VSVG, respectively. When these four plasmids are transfected into 293T human embryonic kidney cells, viral particles accumulate in the supernatant, and the viral product can be concentrated by ultracentrifugation. Lentiviral production protocols are further described in, for example, Tiscornia et al., *Nature Protocols,* 1: 241-245 (2006); Stevenson, M., *Curr. Top. Microbiol. Immunol.,* 261: 1-30 (2002); Cronin et al., *Curr. Gene Ther.,* 5: 387-398 (2005); Sandrin et al., *Curr. Top. Microbiol. Immunol.,* 281: 137-178 (2003); Zufferey, R., *Curr. Top. Microbiol. Immunol.,* 261: 107-121 (2002); Sinn et al., *Gene Ther.,* 12: 1089-1098 (2005); and Saenz, D. T. and Poeschla, E. M., *J. Gene Med.,* 6: S95-S104 (2004). Other methods for producing lentiviral vectors are known in the art and described in, for example, U.S. Patent Application Publications 2008/0254008 and 2010/0003746; and Yang et al., *Hum Gene Ther. Methods,* 23(2): 73-83 (2012).

The invention provides a composition comprising the lentiviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the lentiviral vector. Any suitable carrier can be used within the context of the invention, and such carriers are well known in the art. The choice of carrier will be determined, in part, by the particular use of the composition (e.g., administration to an animal) and the particular method used to administer the composition. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the lentiviral vector is part of a composition formulated to protect the lentiviral vector from damage prior to administration. For example, the composition can be formulated to reduce loss of the lentiviral vector on devices used to prepare, store, or administer lentiviral vector, such as glassware, syringes, or needles. The composition can be formulated to decrease the light sensitivity and/or temperature sensitivity of lentiviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the lentiviral vector, and facilitate its administration. Formulations for lentiviral-containing compositions are further described in, for example, Ausubel et al., *Bioprocess Int,* 10(2): 32-43 (2012), U.S. Pat. No. 7,575,924, and International Patent Application Publication WO 2013/139300.

The invention provides a host cell transduced with the lentiviral vector or composition comprising the lentiviral vector described herein. Preferred host cells are those that can be easily and reliably grown, have reasonably fast growth rates, have well characterized expression systems, and can be transformed, transfected, or transduced easily and efficiently with the inventive lentiviral vector. The host cell can be any suitable eukaryotic cell known in the art including, for example, yeast cells, insect cells, and mammalian cells. Preferably, mammalian cells are utilized in the invention. In one embodiment, the host cells are packaging cells used for producing lentiviral vector particles, including, for example, 293T cells (ATCC No. CRL-3216) and HT1080 cells (ATCC No. CCL-121). In another embodiment, the host cell is a hematopoietic stem cell. Hematopoietic stem cells (HSCs) are multipotent, self-renewing progenitor cells that develop from mesodermal hemangioblast cells. All differentiated blood cells (i.e., myelocytes, lymphocytes, erythrocytes, and platelets) arise from HSCs. HSCs can be found in adult bone marrow, peripheral blood, and umbilical cord blood. In another embodiment, the host cell is a cell that expresses the CD34 protein, which is also referred to as a "CD34+" cell. CD34 is a cell surface glycoprotein that functions as a cell-cell adhesion factor and may also mediate the attachment of stem cells to bone marrow extracellular matrix or directly to stromal cells. CD34 is a marker for primitive blood- and bone marrow-derived progenitor cells, especially for HSCs.

The invention further provides method for treating sickle cell disease (e.g., sickle cell anemia) or thalassemia in a mammal, desirably a human, in need thereof. The method comprises (a) harvesting hematopoietic stem cells from the mammal, (b) transducing the hematopoietic stem cells with the aforementioned lentiviral vector or composition comprising the lentiviral vector, and (c) transplanting the transduced hematopoietic stem cells into in the mammal, whereupon the nucleic acid sequence encoding a human β-globin protein or human γ-globin protein is expressed in the mammal and the sickle cell disease or thalassemia is treated.

As discussed herein, both sickle cell disease and thalassemia occur as a result of mutations in the human β-globin gene locus. In sickle cell disease, hemoglobin S replaces both β-globin subunits in mature hemoglobin, which distorts red blood cells into a sickle, or crescent shape. Sickling of red blood cells induces premature destruction of red blood cells, which leads to anemia. In addition, gamma chain production continues into adulthood in some beta-thalassemias and related conditions, and fetal hemoglobin is protective against complications of sickle-cell anemia. The inventive method can be used to treat any form of sickle cell disease. Thalassemia is an autosomal recessive disorder that is caused by mutations in the alpha globin gene (α-thalassemia), the β-globin gene (β-thalassemia), or less commonly, the δ-globin gene (δ-thalassemia). Thalassemia typically presents as microcytic anemia and causes other complications such as, for example, iron overload, bone deformities, cardiovascular disease, infection, and an enlarged spleen. The inventive method can be used to treat β-thalassemia or δ-thalassemia. Preferably, the inventive method is used to treat β-thalassemia. While the inventive method preferably is used to treat sickle cell disease or β-thalassemia, the inventive method can be used to treat any β-globin abnormality, such as those described herein.

Hematopoietic stem cells can be harvested from bone marrow, peripheral blood, or umbilical cord blood of the mammal (e.g., a human) using methods known in the art, such as those described in, for example, Wognum et al., *Arch Med Res.*, 34(6): 461-75 (2003); Ng et al., *Methods Mol. Biol.*, 506: 13-21 (2009); Weissman and Shizuru, *Blood*, 112(9): 3543-3553 (2008); Frisch and Calvi, *Skeletal Development and Repair Methods in Molecular Biology*, 1130: 315-324 (2014); and U.S. Pat. No. 8,383,404. For example, HSCs can be harvested from the pelvis, at the iliac crest, using a needle and syringe. Alternatively, HSCs can be isolated from circulating peripheral blood by injecting the mammal (or allogeneic donor) with a cytokine, such as granulocyte-colony stimulating factor (G-CSF), that induce cells to leave the bone marrow and circulate in the blood vessels.

The harvested HSCs can be "autologous" or "allogeneic." Autologous HSCs are removed from a mammal, stored (and optionally modified), and returned back to the same mammal. Allogeneic HSCs are removed from a mammal, stored (and optionally modified), and transplanted into a genetically similar, but not identical, recipient. Preferably, the cells are autologous to the mammal.

The inventive lentiviral vector, or composition comprising the inventive lentiviral vector, may be introduced into a hematopoietic cell by "transfection," "transformation," or "transduction." The terms "transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Lentiviral vectors typically are introduced into host cells after growth of infectious particles in suitable packaging cells.

The HSCs may be transduced with the lentiviral vector in vivo or in vitro, depending on the ultimate application. In one embodiment, the HSCs are transduced in vitro with the inventive lentiviral vector or composition comprising the inventive lentiviral vector followed by infusion of the transduced stem cells into the mammal. In this embodiment, the human stem cell can be removed from a human patient using methods well known to in the art and transduced as described above. The transduced HSCs are then reintroduced into the same (autologous) or different mammal (allogeneic).

Once harvested and transduced with the inventive lentiviral vector or composition in vitro, the HSCs are cultured under conditions in which the nucleic acid sequence encoding a human β-globin protein is expressed. HSCs can be cultured using methods known in the art, such as those described in, for example, Csaszar et al., *Cell Stem Cell.*, 10(2): 218-29 (2012); Madlambayan et al., *Biol Blood Marrow Transplant.*, 12(10): 1020-1030 (2006); Woods et al., *Stem Cells*, 29(7): 1158-1164 (2011); U.S. Patent Application Publications 2002/0061293 and 2012/0071397; and International Patent Application Publication WO 2014/043131; or using commercially available systems, such as those available from, for example, Life Technologies Corp., Carlsbad, Calif. and Stem Cell Technologies, Inc., Vancouver, BC.

The inventive method further comprises transplanting the HSCs into a mammal in need thereof. Hematopoietic stem cell transplantation (HSCT) has become the standard of care for many patients with certain congenital or acquired disorders of the hematopoietic system or with chemosensitive, radiosensitive, or immunosensitive malignancies (see, e.g., Gratwohl et al., *JAMA*, 303(16): 1617-1624 (2010); and Copelan, E. A., *NEJM*, 354: 1813-1826 (2006)). Methods of isolating stem cells from a subject, transducing them with a therapeutic gene (e.g., an anti-sickling human β-globin gene), and returning the modified stem cells to the subject are well known in the art (see, e.g., Pawliuk et al., *Science*, 294(5550): 2368-2371 (2001); Tyndall et al., *Bone Marrow Transplant*, 24 (7): 729-34 (1999); and Burt et al., *JAMA*, 299 (8): 925-36 (2008)). Other methods for transplanting HSCs into a subject in need thereof that can be used in the inventive method include those used, for example, for bone marrow transplantation or peripheral blood stem cell transplantation.

Expression of the human β-globin gene and human γ-globin gene can be determined at the level of transcription or translation. In one embodiment, human β-globin or γ-globin messenger RNA (mRNA) levels can be quantified by any suitable method known in the art, such as, for example, Northern blotting, reverse transcription polymerase chain reaction (RT-PCR), RT quantitative PCR (RT-qPCR), quantitative PCR, serial analysis of gene expression (SAGE), or microarrays. In another embodiment, human β-globin or γ-globin protein levels can be measured using suitable methods known in the art. Such methods include, for example, Western blot, radioimmunoassay (RIA), and ELISA.

In another embodiment, the hematopoietic stem cells can be transduced with the lentiviral vector in vivo by directly injecting into a mammal in need thereof the aforementioned composition comprising the lentiviral vector and a carrier therefor (e.g., a pharmaceutically acceptable carrier). The composition comprising the lentiviral vector can be administered to a mammal using standard administration techniques, and is preferably suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

The inventive method results in the treatment sickle cell disease or thalassemia in the mammal. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the transduced HSCs (when the HSCs are transduced in vitro) or the composition comprising the inventive lentiviral vector (when the HSCs are transduced in vivo). A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the transduced HSC's and encoded β-globin protein or γ-globin protein to elicit a desired response in the individual. For example, a therapeutically effective amount of transduced HSCs of the invention is an amount which results in expression of non-sickling (e.g., wild-type) human β-globin or human γ-globin at levels that ameliorates or reverses sickle cell disease or thalassemia in a human.

The dose of lentiviral vector delivered to hematopoietic stem cells, either by in vitro or in vivo methods, typically can be, for example, a multiplicity of infection (MOI) in the range of 1 to 100 (e.g., 1, 5, 10, 15, 20, 25, 30, 35, 40, 45, 50, 55, 60, 65, 70, 75, 80, 85, 90, 95, 100 MOI, or a range defined by any two of the forgoing values); however, doses below or above this exemplary range are within the scope of the invention.

Alternatively, the pharmacologic and/or physiologic effect may be prophylactic, i.e., the effect completely or partially prevents a disease or symptom thereof. In this respect, the inventive method comprises administering a "prophylactically effective amount" of the transduced HSCs or the composition comprising the inventive lentiviral vector. A "prophylactically effective amount" refers to an amount effective, at dosages and for periods of time necessary, to achieve a desired prophylactic result (e.g., prevention of disease onset).

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition or by multiple bolus administrations of the composition.

The transduced HSCs or the composition comprising the inventive lentiviral vector may be provided to a mammal alone or in combination with other drugs (e.g., as an adjuvant). For example, the transduced HSCs or the composition comprising the inventive lentiviral vector can be administered in combination with other agents for the treatment or prevention of sickle cell disease or thalassemia (e.g., acetaminophen, nonsteroidal anti-inflammatory drugs (NSAIDS), hydroxyurea, antibiotics, and/or folic acid supplements). Alternatively, the transduced HSCs can be administered in combination with other agents that reduce or prevent one or more complications associated with HSC transplantation. Such complications include, for example, infections, sepsis, mucositis, and graft-versus-host-disease (GVHD). In this respect, the transduced HSCs can be used in combination with antiviral agents, anticoagulants (e.g., defibrotide), ursodeoxycholic acid, and/or corticosteroids (e.g., prednisone).

In another embodiment, the inventive method for treating sickle cell disease or thalassemia in a mammal can be performed in conjunction with other therapeutic regimens used to treat sickle cell disease or thalassemia or complications thereof. In this respect, the inventive method can be performed in conjunction with, for example, blood transfusions and/or iron chelation therapy.

In addition, the inventive lentiviral vector construct can be used as a template in gene correction strategies for sickle cell disease and β-thalassemia.

The following examples further illustrate the invention but, of course, should not be construed as in any way limiting its scope.

Example 1

This example demonstrates the preparation of an inventive lentiviral vector comprising a forward-oriented nucleic acid sequence encoding a human β-globin protein, which can be grown at higher titers and transduces cells more efficiently than currently available reverse-oriented lentiviral vectors.

Plasmid Construction

To construct forward-oriented β-globin-expressing HIV-1 vector plasmids, a β-globin expression cassette was excised from a reverse-oriented globin-expressing lentiviral vector plasmid (May et al, Nature, 406: 82-86 (2000)), and the expression cassette was inserted into the same vector backbone in a forward orientation (i.e., 5' to 3') with respect to the lentiviral genome. The resulting forward-oriented β-globin-expressing plasmids were optimized by including locus control region (LCR) elements, the native β-globin promoter, and a 3' untranslated region (3'UTR) lacking the polyadenylation (poly A) signal. To positively select β-globin gene vectors that contain intron 2, the rev response element (RRE) was deleted from the forward-oriented vector genome, and then inserted into intron 2 off β-globin gene.

HIV-1 Based Lentiviral Vector Preparation

Lentiviral vectors were generated using a chimeric HIV-1 based lentiviral vector system (χHIV vector) described in Uchida et al., J. Virol., 83: 9854-9862 (2009), in which HIV-1 genomes are packaged into the simian immunodeficiency virus (SIV) capsid. Specifically, self-inactivating (SIN) chimeric HIV-1 vector plasmids were prepared in 10-cm dishes by cotransfection of 293T cells in various combinations with plasmids expressing Gag/Pol, Rev/Tat, and vesicular stomatitis virus glycoprotein envelope (VSVG) proteins (see, e.g., Uchida et al., J. Nippon Med. Sch., 76: 134-147 (2009)). The HIV-1 vector plasmids contained erythroid-specific expression cassettes in both forward and reverse orientations comprising genes encoding enhanced green fluorescent protein (GFP), enhanced yellow fluorescent protein (YFP), or human β-globin. An HIV-1 vector plasmid comprising a GFP gene under the control of a murine stem cell virus promoter was used as a control. The lentiviral vectors were concentrated 100-fold by ultracentrifugation (Beckman Coulter, Brea, Calif.) (see, e.g., Kutner et al., Nat. Protoc., 4: 495-505 (2009)). The HIV-1 vector system was provided by Dr. Arthur Nienhuis (St. Jude Children's Research Hospital, Memphis, Tenn., USA) (see also Hanawa et al., Mol. Ther., 5: 242-251 (2002)).

Titers of lentiviral vectors were evaluated using HeLa or MEL cell lines as described in Uchida et al., Mol. Ther., 19: 133-139 (2011). Specifically, $1\times10^5$ cells were transduced with lentiviral vectors in 1 mL media containing 8 µg/ml polybrene (Sigma-Aldrich, St. Louis, Mo.). Three to four days after transduction, GFP expression was detected by flow cytometry (FACSCALIBUR™; BD Biosciences, Franklin Lakes, N.J.), and the viral titers were calculated by infectious units (GFP positivity) per mL (vector volume). For β-globin-expressing vectors, genomic DNA was extracted 5-6 days after transduction, and vector copy numbers were evaluated by real time PCR (see, e.g., Uchida et al., Mol. Ther. Nucleic Acids, 2: e122 (2013)). Viral titers were calculated against the GFP-expressing control vector. The titers of the inventive forward-oriented β-globin expressing vector were approximately 10-fold higher than a reverse-oriented vector, and were comparable to the GFP-expressing control vector.

The results of this example confirm the preparation of a β-globin-expressing lentiviral vector of the invention.

Example 2

This example demonstrates a method of transducing human CD34+ cells with an inventive lentiviral vector expressing β-globin.

Figure 1:
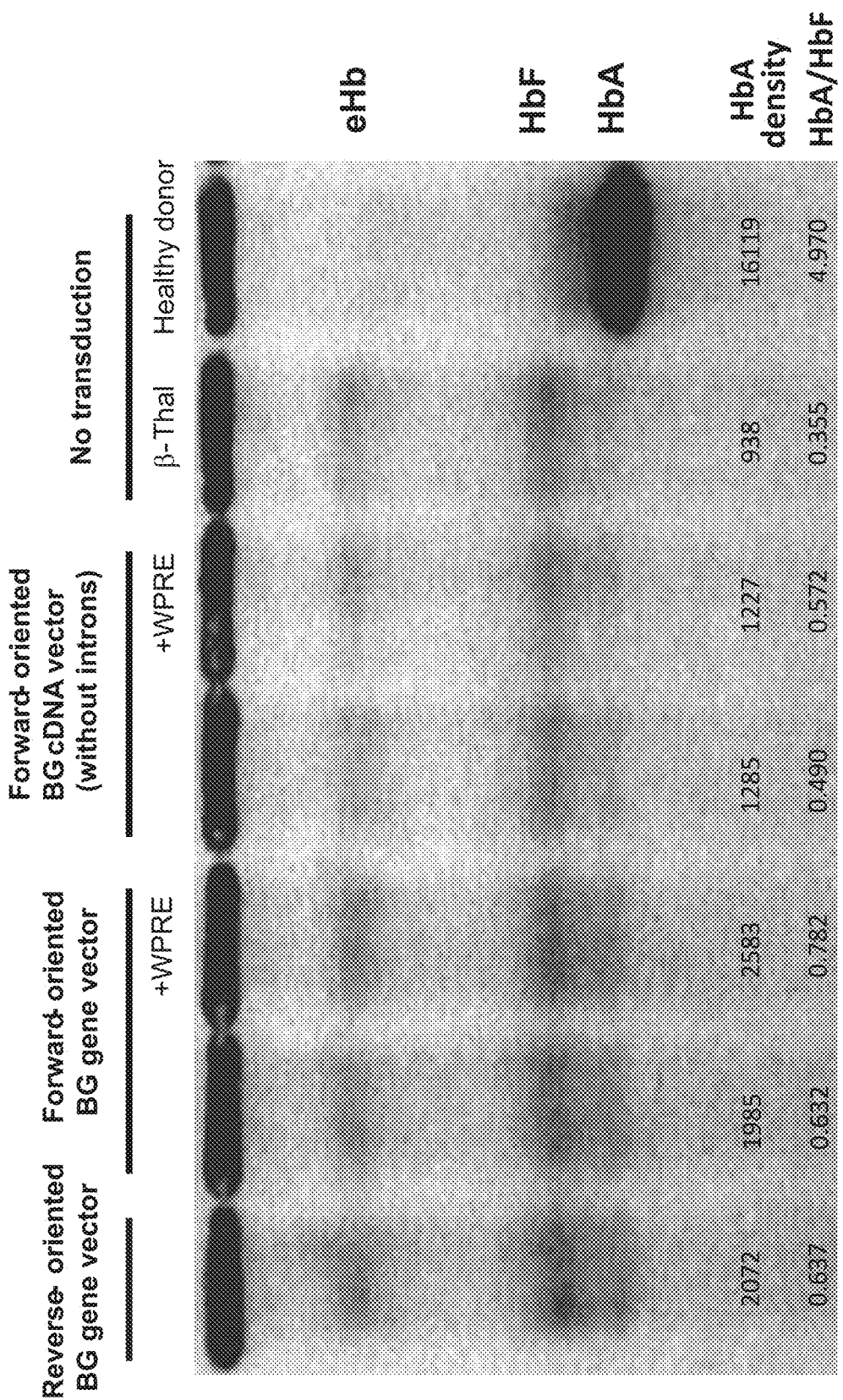
Figure 2A:
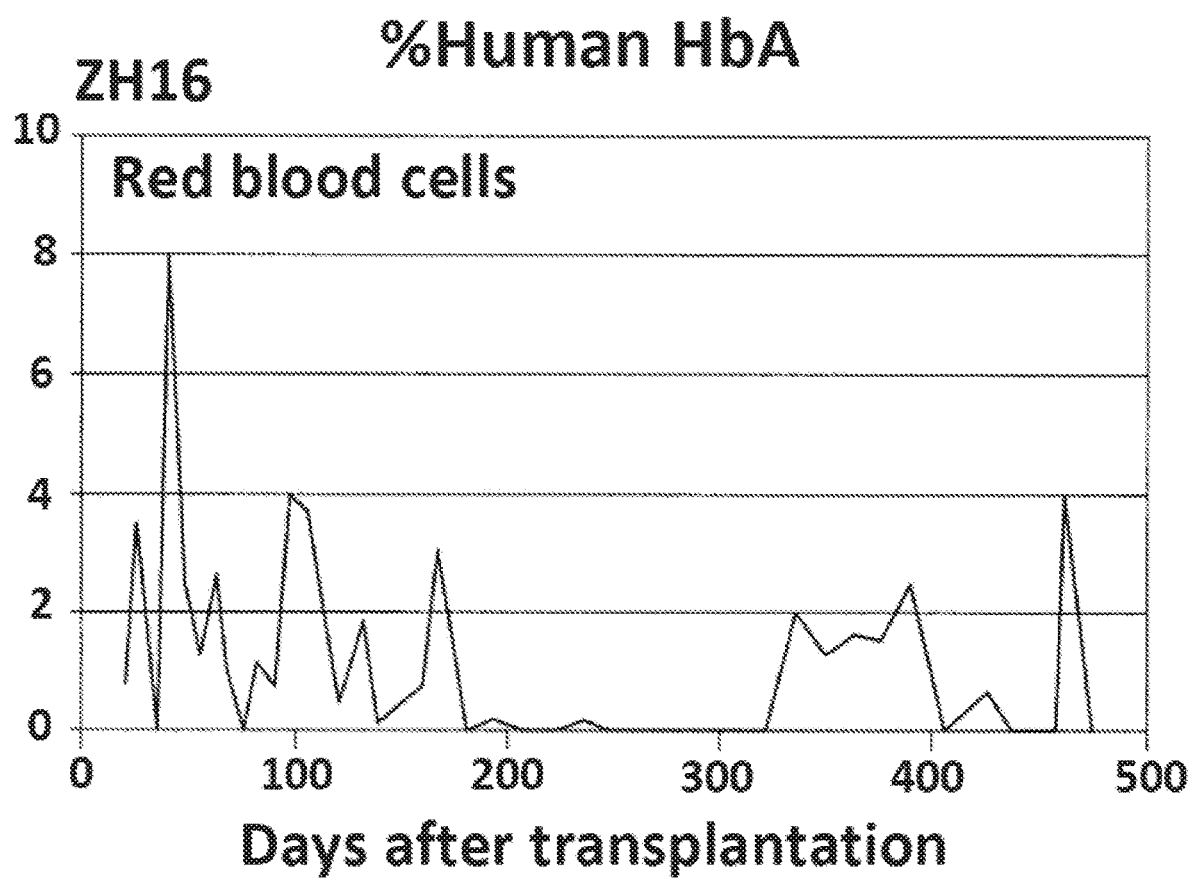
FIG. 2A is a graph depicting experimental results illustrating human hemoglobin A expression in a rhesus monkey (ZH16) transplanted with rhesus CD34+ cells transduced with an inventive lentiviral vector expressing β-globin.
Figure 2B:
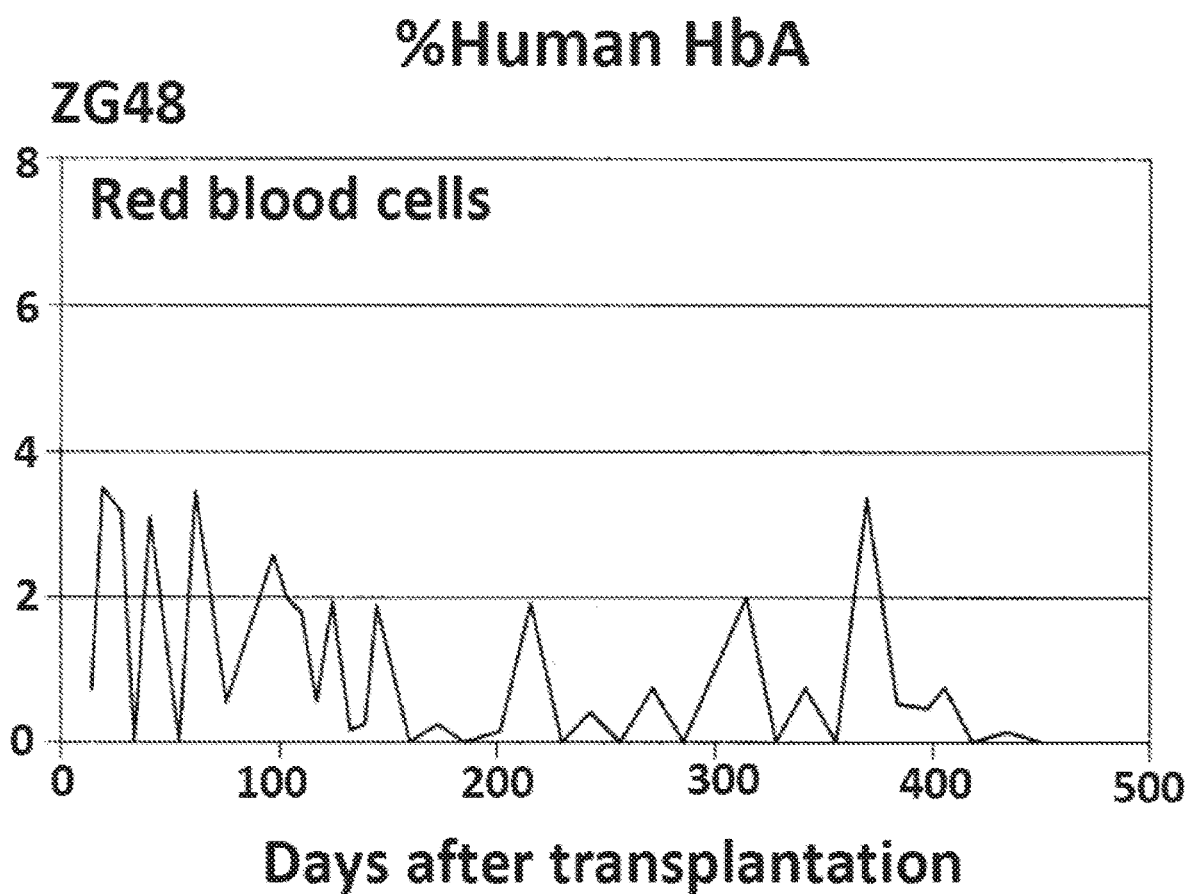
FIG. 2B is a graph depicting experimental results illustrating human hemoglobin A expression in a rhesus monkey (ZG48) transplanted with rhesus CD34+ cells transduced with an inventive lentiviral vector expressing β-globin.
Figure 2C:
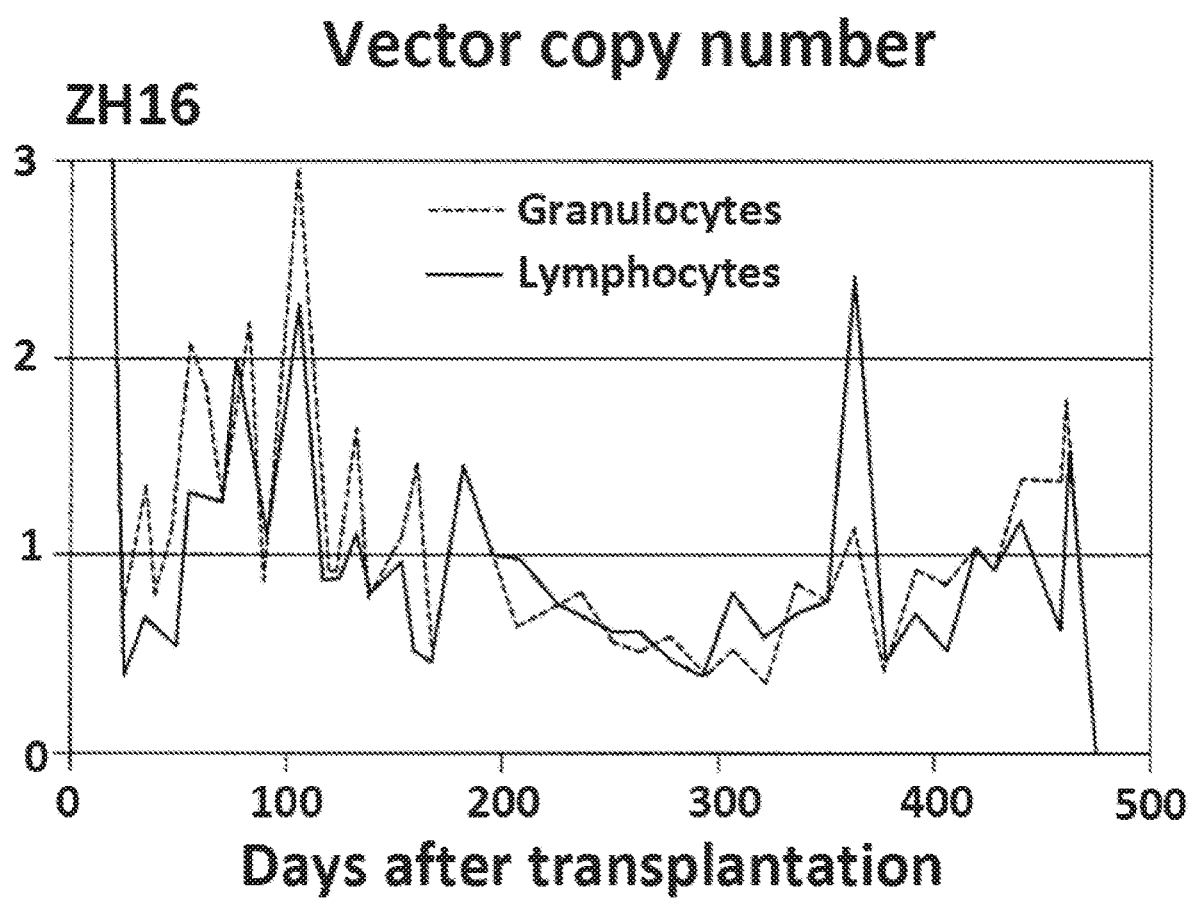
FIG. 2C is a graph depicting experimental results illustrating lentiviral vector copy number in a rhesus monkey (ZH16) transplanted with rhesus CD34+ cells transduced with an inventive lentiviral vector expressing β-globin.
Figure 2D:
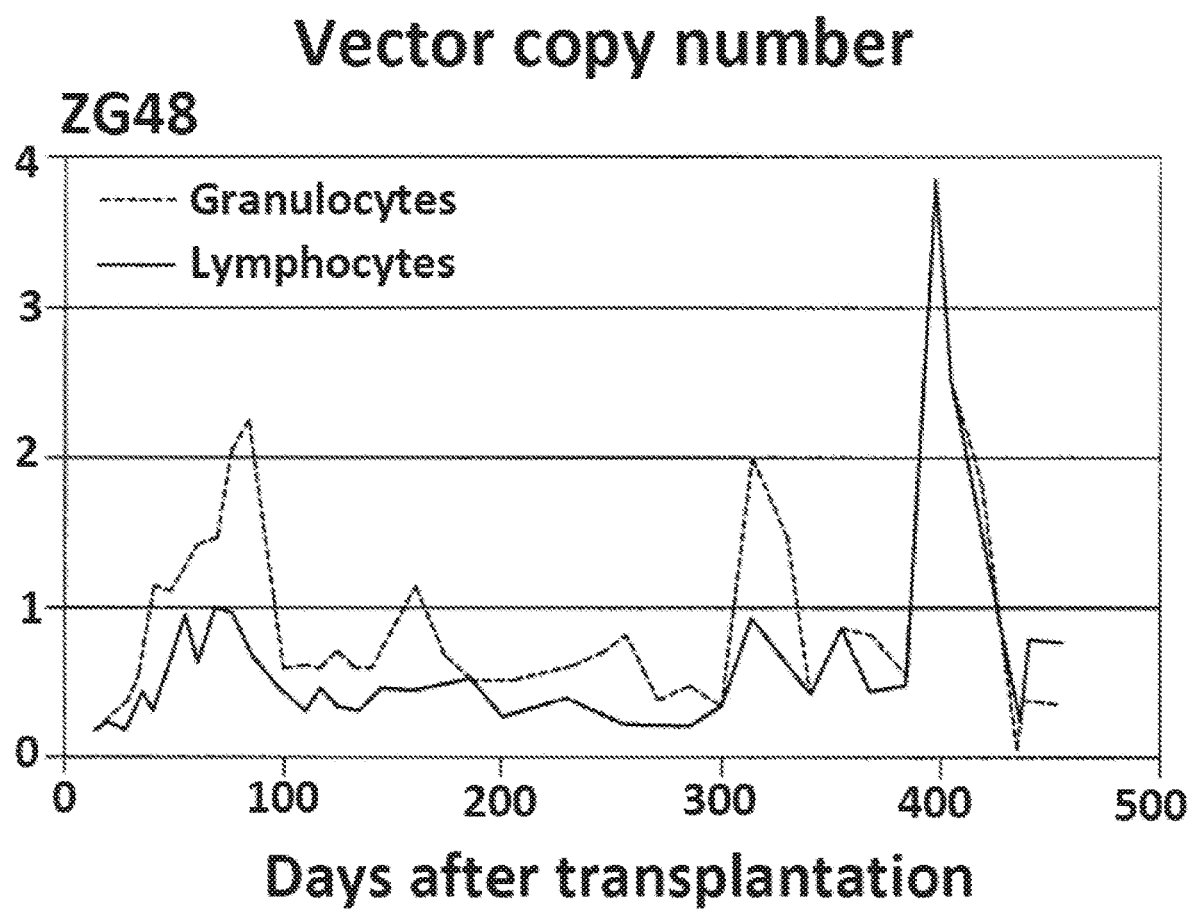
FIG. 2D is a graph depicting experimental results illustrating lentiviral vector copy number in a rhesus monkey (ZG48) transplanted with rhesus CD34+ cells transduced with an inventive lentiviral vector expressing β-globin.

$1 \times 10^5$ human CD34+ cells obtained from β-thalassemia patients were cultured on fibronectin-coated (RETRONECTIN™, TaKaRa, Otsu, Shiga, Japan) 12-well plates in 1 mL serum-free X-VIVO10 media (Lonza, Allendale, N.J.) containing stem cell factor (SCF), FMS-like tyrosine kinase 3 ligand (FLT3L), and thrombopoietin (TPO) (all 100 ng/ml; R&D Systems, Minneapolis, Minn.) (see, e.g., Uchida et al., Gene Ther., 18: 1078-1086 (2011)). After overnight prestimulation, CD34+ cells were transduced with the β-globin-expressing lentiviral vectors described in Example 1 at a multiplicity of infection (MOI) of 50 in fresh media containing SCF, FLT3L, and TPO. 24 hours later, transduced cells were differentiated into erythroid cells using erythropoietin for two weeks, as described in Migliaccio et al., Blood Cells Mol. Dis., 28: 169-180 (2002). Hemoglobin A expression was evaluated by hemoglobin electrophoresis (Helena Chemical Company, Collierville, Tenn.). The differentiated human erythroid cells efficiently expressed β-globin from the inventive forward-oriented lentiviral vector, as shown in FIG. 1.

The results of this example demonstrate that the inventive lentiviral vector mediates high levels of β-globin expression in human erythroid cells derived from CD34+ HSCs.

Example 3

This example demonstrates a hematopoietic stem cell transplantation method using rhesus CD34+ cells transduced with an inventive lentiviral vector expressing β-globin.

Granulocyte-colony stimulating factor (G-CSF) and SCF-mobilized rhesus CD34+ cells were cultured in X-VIVO10 media containing SCF, FLT3L, and TPO on fibronectin-coated flasks (Uchida et al., J. Virol., 83: 9854-9862 (2009)). After overnight prestimulation, CD34+ cells were transduced with the lentiviral vectors described in Example 1 (MOI=50) in fresh media containing SCF, FLT3L, and TPO for 24 hours. The transduced CD34+ cells were infused into irradiated rhesus macaques (10 Gy total body irradiation). After engraftment of transduced cells, expression of GFP, YFP, and human β-globin were evaluated by flow cytometry, while vector copy numbers were evaluated by real time PCR.

In two animals, GFP and YFP expression from both forward- and reverse-oriented lentiviral vectors was detected in red blood cells, but not in granulocytes, lymphocytes, and platelets. The forward-oriented lentiviral vector produced approximately 10-fold higher gene expression for two years compared to a comparable reverse-oriented vector, as confirmed by real-time PCR. Human β-globin expression was detected in rhesus hematopoietic repopulating cells following transplantation of the transduced CD34+ cells, as shown in FIGS. 2A-2D.

The results of this example demonstrate that rhesus CD34+ cells transduced with an inventive lentiviral vector efficiently express human β-globin following transplantation into a mammal.

Example 4

This example demonstrates a method of transducing human CD34+ cells with an inventive lentiviral vector expressing γ-globin.

Figure 3:
FIG. 3 is a diagram depicting the γ-globin-expressing lentiviral vector described in Example 4. "LTR" denotes long terminal repeat; "Ψ" denotes the packaging sequence; "LCR" denotes locus control region; "P" denotes β-globin promoter; "3' UTR" denotes 3' untranslated region; "WPRE" denotes woodchuck hepatitis virus post-transcriptional regulatory element.

Using methods similar to those described in Example 1, a forward-oriented lentiviral vector comprising a codon-optimized nucleic acid sequence encoding a human γ-globin protein operably linked to a native human β-globin promoter and a woodchuck hepatitis virus post-transcriptional regulatory element (WPRE) was generated. A map of the γ-globin-expressing lentiviral vector is set forth in FIG. 3. $1 \times 10^5$ human CD34+ cells obtained from a healthy donor were cultured on fibronectin-coated 12-well plates and differentiated into erythroid cells using erythropoietin for two weeks, as described in Migliaccio et al., Blood Cells Mol. Dis., 28: 169-180 (2002). Two days after erythroid differentiation, the cells were transduced with the γ-globin-expressing lentiviral vector (MOI=50). Hemoglobin F expression was evaluated by hemoglobin electrophoresis. The differentiated human erythroid cells efficiently expressed γ-globin from the inventive forward-oriented lentiviral vector, as shown in FIG. 4.

The results of this example demonstrate that the inventive lentiviral vector mediates high levels of γ-globin expression in human erythroid cells derived from CD34+ HSCs.

Example 5

This example demonstrates a hematopoietic stem cell transplantation method using rhesus CD34+ cells transduced with an inventive lentiviral vector expressing γ-globin.

G-CSF and SCF-mobilized rhesus CD34+ cells were cultured in X-VIVO10 media containing SCF, FLT3L, and TPO on fibronectin-coated flasks (Uchida et al., J. Virol., 83: 9854-9862 (2009)). After overnight prestimulation, CD34+ cells were transduced with the lentiviral vectors described in Example 4 (MOI=50) in fresh media containing SCF, FLT3L, and TPO for 24 hours. The transduced CD34+ cells were infused into irradiated rhesus macaques (10 Gy total body irradiation). After engraftment of transduced cells, γ-globin expression was evaluated by flow cytometry, while vector copy numbers were evaluated by real time PCR.

In two animals, γ-globin expression was detected in rhesus hematopoietic repopulating cells following transplantation of the transduced CD34+ cells, as measured by hemoglobin F expression and shown in FIGS. 5A-5D.

The results of this example demonstrate that rhesus CD34+ cells transduced with the inventive lentiviral vector efficiently express human γ-globin following transplantation into a mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A lentiviral vector comprising a nucleic acid sequence encoding a human γ-globin protein operably linked to a native human β-globin gene promoter and a woodchuck hepatitis virus post-transcriptional regulatory element (WPRE), wherein the nucleic acid sequence is oriented from 5' to 3' relative to the lentiviral genome.

2. The lentiviral vector of claim 1, which comprises the following elements in sequence from 5' to 3' relative to the lentiviral genome:
   (a) a first long terminal repeat (LTR),
   (b) a packaging signal,
   (c) a locus control region (LCR),
   (d) the native human β-globin gene promoter,
   (e) the nucleic acid sequence encoding a human γ-globin protein,
   (f) a 3' untranslated region (UTR),
   (g) the WPRE, and
   (h) a second LTR.

3. The lentiviral vector of claim 1, wherein the nucleic acid sequence is codon-optimized.

4. A composition comprising the lentiviral vector of claim 1 and a pharmaceutically acceptable carrier.

5. A host cell transduced with the lentiviral vector of claim 1.

6. The host cell of claim 5, which is a hematopoietic stem cell.

7. The host cell of claim 6, wherein the hematopoietic stem cell is a CD34+ cell.

8. The host cell of claim 5, which is a 293T cell.

9. A lentiviral vector comprising a nucleic acid sequence encoding a human γ-globin protein operably linked to a native human β-globin gene promoter, wherein the nucleic acid sequence is oriented from 5' to 3' relative to the lentiviral genome, wherein the endogenous Rev response element (RRE) of the lentiviral genome is deleted and inserted into intron 2 of the nucleic acid sequence encoding the human γ-globin protein.

10. The lentiviral vector of claim 9, wherein the nucleic acid sequence is codon-optimized.

11. A composition comprising the lentiviral vector of claim 9 and a pharmaceutically acceptable carrier.

12. A host cell transduced with the lentiviral vector of claim 9.

13. The host cell of claim 12, which is a hematopoietic stem cell.

14. A method for treating sickle cell disease or thalassemia in a mammal in need thereof, which method comprises:
   (a) harvesting hematopoietic stem cells from an allogeneic or an autologous mammal,
   (b) transducing the hematopoietic stem cells with a composition comprising (1) a lentiviral vector comprising a nucleic acid sequence encoding a human β-globin protein or a human γ-globin protein and operably linked to a native human β-globin gene promoter, wherein (i) the nucleic acid sequence is oriented from 5' to 3' relative to the lentiviral genome and (ii) the endogenous RRE of the lentiviral genome is deleted and inserted into intron 2 of the nucleic acid sequence and (2) a pharmaceutically acceptable carrier, and
   (c) transplanting the transduced hematopoietic stem cells into the mammal in need thereof, whereupon the nucleic acid sequence encoding a human β-globin protein or a human γ-globin protein is expressed in the mammal and the sickle cell disease or the thalassemia is treated.

15. The method of claim 14, wherein the mammal in need thereof is a human.

16. The method of claim 15, wherein the human has sickle cell disease.

17. The method of claim 16, wherein the human has sickle cell anemia.

18. The method of claim 15, wherein the human has thalassemia.

19. The method of claim 18, wherein the thalassemia is β-thalassemia.

20. The method of claim 14, wherein the hematopoietic stem cells are CD34+ cells.

* * * * *